United States Patent
Enriquez et al.

(10) Patent No.: US 7,736,000 B2
(45) Date of Patent: Jun. 15, 2010

(54) METHOD AND APPARATUS FOR TRACKING EYE MOVEMENT

(75) Inventors: Mario Enriquez, Richmond (CA); Colin Swindells, Victoria (CA); Ricardo Pedrosa, Vancouver (CA)

(73) Assignee: Locarna Systems, Inc., Victoria (CA)

( * ) Notice: Subject to any disclaimer, the term of this patent is extended or adjusted under 35 U.S.C. 154(b) by 0 days.

(21) Appl. No.: 12/392,574

(22) Filed: Feb. 25, 2009

(65) Prior Publication Data

US 2010/0053555 A1  Mar. 4, 2010

Related U.S. Application Data

(60) Provisional application No. 61/092,299, filed on Aug. 27, 2008.

(51) Int. Cl.
   *A61B 3/14* (2006.01)
   *A61B 3/10* (2006.01)
   *A61B 3/00* (2006.01)

(52) U.S. Cl. .................. 351/210; 351/205; 351/246

(58) Field of Classification Search ......... 351/209–211, 351/205–206, 200, 246
See application file for complete search history.

(56) References Cited

U.S. PATENT DOCUMENTS

| | | | |
|---|---|---|---|
| 4,852,988 A * | 8/1989 | Velez et al. ........... 351/210 |
| 5,016,282 A | 5/1991 | Tomono et al. |
| 6,873,714 B2 | 3/2005 | Witt et al. |
| 7,130,447 B2 | 10/2006 | Aughey et al. |
| 7,306,337 B2 | 12/2007 | Ji et al. |
| 7,331,671 B2 | 2/2008 | Hammoud |
| 7,365,738 B2 | 4/2008 | Molander et al. |
| 7,391,887 B2 | 6/2008 | Durnell |
| 7,396,129 B2 | 7/2008 | Endrikhovski et al. |
| 7,401,920 B1 | 7/2008 | Kranz et al. |
| 2005/0225723 A1 | 10/2005 | Pilu |

* cited by examiner

*Primary Examiner*—Scott J Sugarman
*Assistant Examiner*—Dawayne A Pinkney
(74) *Attorney, Agent, or Firm*—Fasken Martineau DuMoulin LLP

(57) ABSTRACT

An eye tracking apparatus includes a first image detector for capturing scene images, a second image detector fixed relative to the first image detector for capturing eye images including a pupil of a person and a reference object located within an image detection field, a processor for receiving the scene images and the eye images and outputting eye tracking images, each of the eye tracking images including a gaze point corresponding to a line of sight of the person, the processor for determining a location of the gaze point based on a calibration mapping that maps pupil location within the image detection field to the scene images and a correction mapping that corrects for movement of the reference object within the image detection field of the second image detector. Wherein the first image detector and the second image detector are coupled to a wearable accessory and movement of the reference object within the image detection field corresponds to movement of the wearable accessory relative to the person.

8 Claims, 5 Drawing Sheets

METHOD AND APPARATUS FOR TRACKING EYE MOVEMENT

TECHNICAL FIELD

The present invention relates to head-mounted eye tracking devices.

BACKGROUND

Eye tracking devices for determining where a person is looking at a given time are well known in the art. Such devices typically include a first video camera for capturing a scene and a second video camera for capturing eye movement of the person. The video streams are processed to produce a single video, which shows the scene and includes a pointer that identifies where the person is looking at any given time.

In general, eye tracking devices are calibrated prior to use in order to establish a mapping between the eye coordinates as they appear in the second video camera image and the scene image. Often, re-calibration is required when changes in environmental circumstances, such as ambient light levels, for example, occur.

Eye tracking devices that are worn as accessories by the person, such as eye glasses or helmets, for example, often slip, get bumped or are removed. All of these actions reduce the accuracy of an eye tracking device because the mapping between the eye camera and scene camera generally becomes less accurate as a worn accessory is moved from its originally calibrated location.

The calibration process is time consuming and requires a directed effort by the person. It is therefore desirable to provide a method and apparatus for maintaining calibration of an eye tracking apparatus.

SUMMARY

In one aspect, there is provided herein a method of correcting for movement of a reference object within an image detection field of an eye tracking apparatus, the method including: providing the eye tracking apparatus, the eye tracking apparatus including a first image detector for capturing scene images, a second image detector for capturing eye images including a pupil of the person and a processor for receiving the scene images and the eye images and outputting eye tracking images, each of the eye tracking images including a gaze point corresponding to a line of sight of the person, the first image detector and the second image detector being coupled to a wearable accessory and being fixed relative to one another; mounting the wearable accessory on the person; identifying the reference object, the reference object being located within the image detection field of the second image detector; performing a calibration method and generating a calibration mapping, the calibration mapping for mapping pupil location within the image detection field to the scene images; capturing the scene images and the eye images; determining a location of the reference object within the image detection field on each of the eye images; applying the calibration mapping to each of the eye tracking images and adjusting the gaze point on each of the eye tracking images to correct for movement of the reference object within the image detection field; wherein movement of the reference object within the image detection field corresponds to movement of the wearable accessory relative to the person.

In another aspect, there is provided herein an eye tracking apparatus including: a first image detector for capturing scene images; a second image detector for capturing eye images including a pupil of a person and a reference object located within an image detection field, the second image detector being fixed relative to the first image detector; a processor for receiving the scene images and the eye images and outputting eye tracking images, each of the eye tracking images including a gaze point corresponding to a line of sight of the person, the processor for determining a location of the gaze point based on a calibration mapping that maps pupil location within the image detection field to the scene images and a correction mapping that corrects for movement of the reference object within the image detection field of the second image detector; wherein the first image detector and the second image detector are coupled to a wearable accessory and movement of the reference object within the image detection field corresponds to movement of the wearable accessory relative to the person.

DRAWINGS

The following figures set forth embodiments of the invention in which like reference numerals denote like parts. Embodiments of the invention are illustrated by way of example and not by way of limitation in the accompanying figures.

Figure 1:
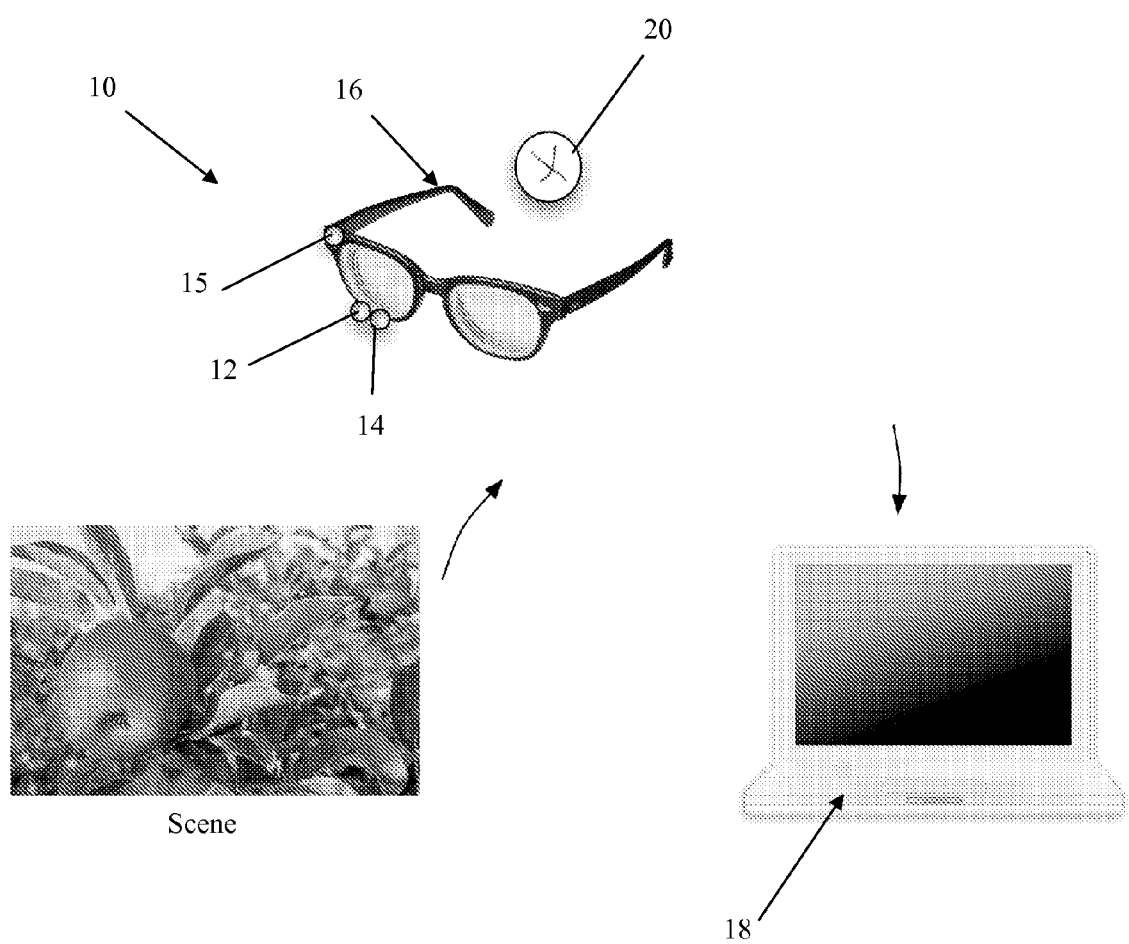
FIG. 1 is a schematic diagram of an eye tracking apparatus according to an embodiment of the invention.
Figure 4:
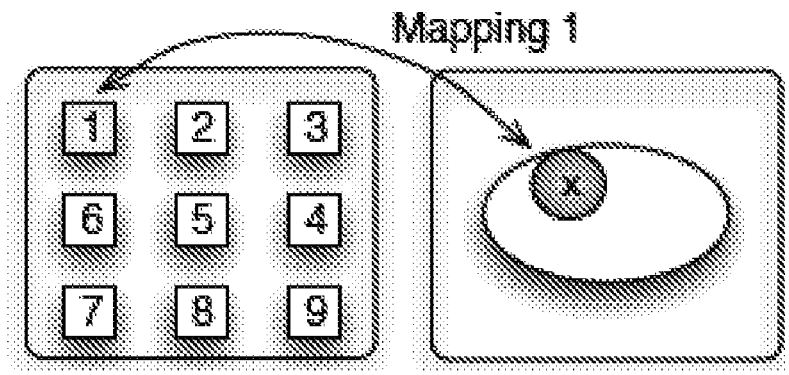
Figure 4:
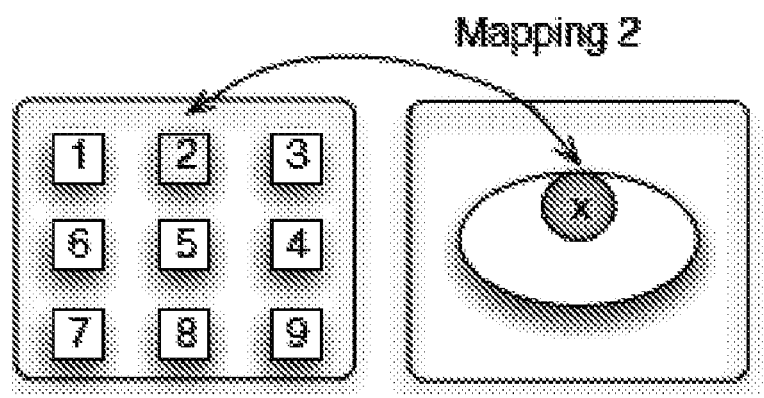
Figure 4:
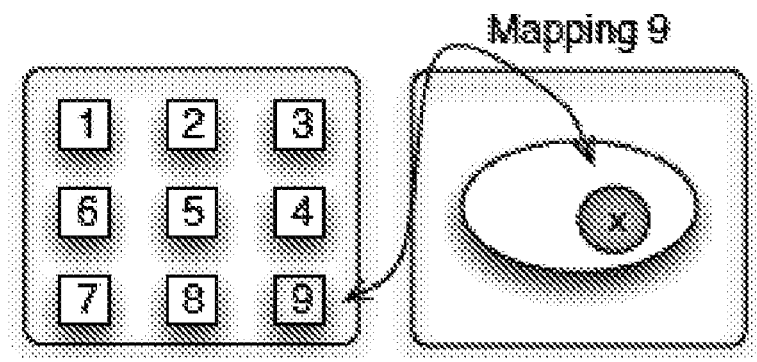
Figure 5:
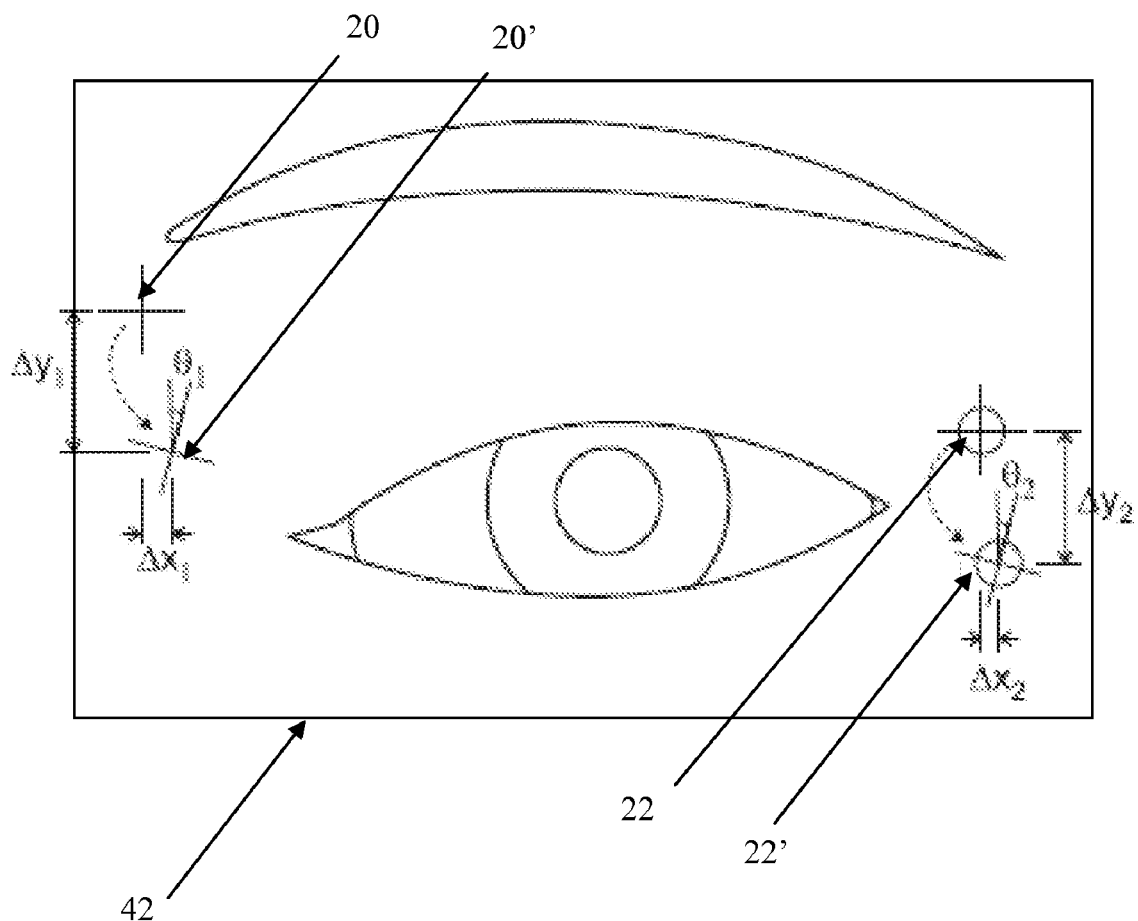

FIGS. 4(a), 4(b) and 4(c) are schematic views representing an example calibration method; and FIG. 5 is a schematic view of an image captured by an eye camera of the eye tracking apparatus of FIG. 1.

DETAILED DESCRIPTION OF EMBODIMENTS OF THE INVENTION

Referring to FIG. 1, an eye tracking apparatus 10 is generally shown. The eye tracking apparatus 10 includes a first image detector 12 for capturing scene images, a second image detector 14 for capturing eye images including a pupil of a person and a reference object located within an image detection field, the second image detector 14 being fixed relative to the first image detector 12, a processor for receiving the scene images and the eye images and outputting eye tracking images, each of the eye tracking images including a gaze point corresponding to a line of sight of the person, the processor for determining a location of the gaze point based on a calibration mapping that maps pupil location within the image detection field to the scene images and a correction mapping that corrects for movement of the reference object within the image detection field of the second image detector. The first image detector 12 and the second image detector 14 are coupled to a wearable accessory 16 and movement of the reference object within the image detection field corresponds to movement of the wearable accessory 16 relative to the person.

In one embodiment, the first and second image detectors 12, 14 are first and second video cameras, respectively, that are mounted on the wearable accessory 16, which is a pair of eye glasses. The scene camera 12 captures video frames of an object in a scene, such as the apple of FIG. 1, for example. At the same time as the scene camera 12 captures video frames of objects, the eye camera 14 captures video frames including a person's eye and surrounding facial features.

Video captured using the scene camera 12 and the eye camera 14 is received by a computer 18, which includes a processor (not shown). The processor executes software that is stored in a computer memory. The software includes computer code for merging the scene video and the eye video to produce a single eye tracking video that includes eye gaze coordinates provided on each video frame. The software also includes computer code for correcting for movement of a reference object within an image detection field of the eye tracking apparatus 10, as will be further described in relation to FIG. 2. Techniques for merging scene video and eye video are well known in the art and any suitable merging process may be used.

The computer 18 shown in FIG. 1 is a laptop computer. The computer 18 may alternatively be a desktop computer or any mobile electronic device such as a PDA (Personal Digital Assistant) or a cellular phone, for example. The computer 18 communicates with the cameras 12, 14 via a cable (not shown) or a wireless connection.

In another embodiment, a portable media storage device (not shown) is provided to receive video data from the scene camera 12 and the eye camera 14 and forward the video data to the computer 18. Communication between the computer 18 and the portable media storage device occurs via a cable (not shown) that is selectively connected therebetween or via a wireless connection.

It will be appreciated by a person skilled in the art that the eye tracking apparatus 10 may further include a microphone 15 for capturing sounds from the environment. In addition, the eye tracking apparatus 10 may include more than one scene camera 12 and more than one eye camera 14.

A method 24 of correcting for movement of a reference object within an image detection field of the eye tracking apparatus 10 is provided herein. The method generally includes: providing an eye tracking apparatus including a first image detector for capturing scene images, a second image detector for capturing eye images including a pupil of a person and a processor for receiving the scene images and the eye images and outputting eye tracking images, each of the eye tracking images including a gaze point corresponding to a line of sight of the person, the first image detector and the second image detector being coupled to a wearable accessory and being fixed relative to one another, mounting the wearable accessory on the person, identifying a reference object, the reference object being located within the image detection field of the second image detector, performing a calibration method and generating a calibration mapping to map pupil location within the image detection field to the scene images, capturing the scene images and the eye images, determining a location of the reference object within the image detection field on each of the eye images, applying the calibration mapping to each of the eye tracking images and adjusting the gaze point on each of the eye tracking images to correct for movement of the reference object within the image detection field. Movement of the reference object within the image detection field corresponds to movement of the wearable accessory relative to the person.

Figure 2:
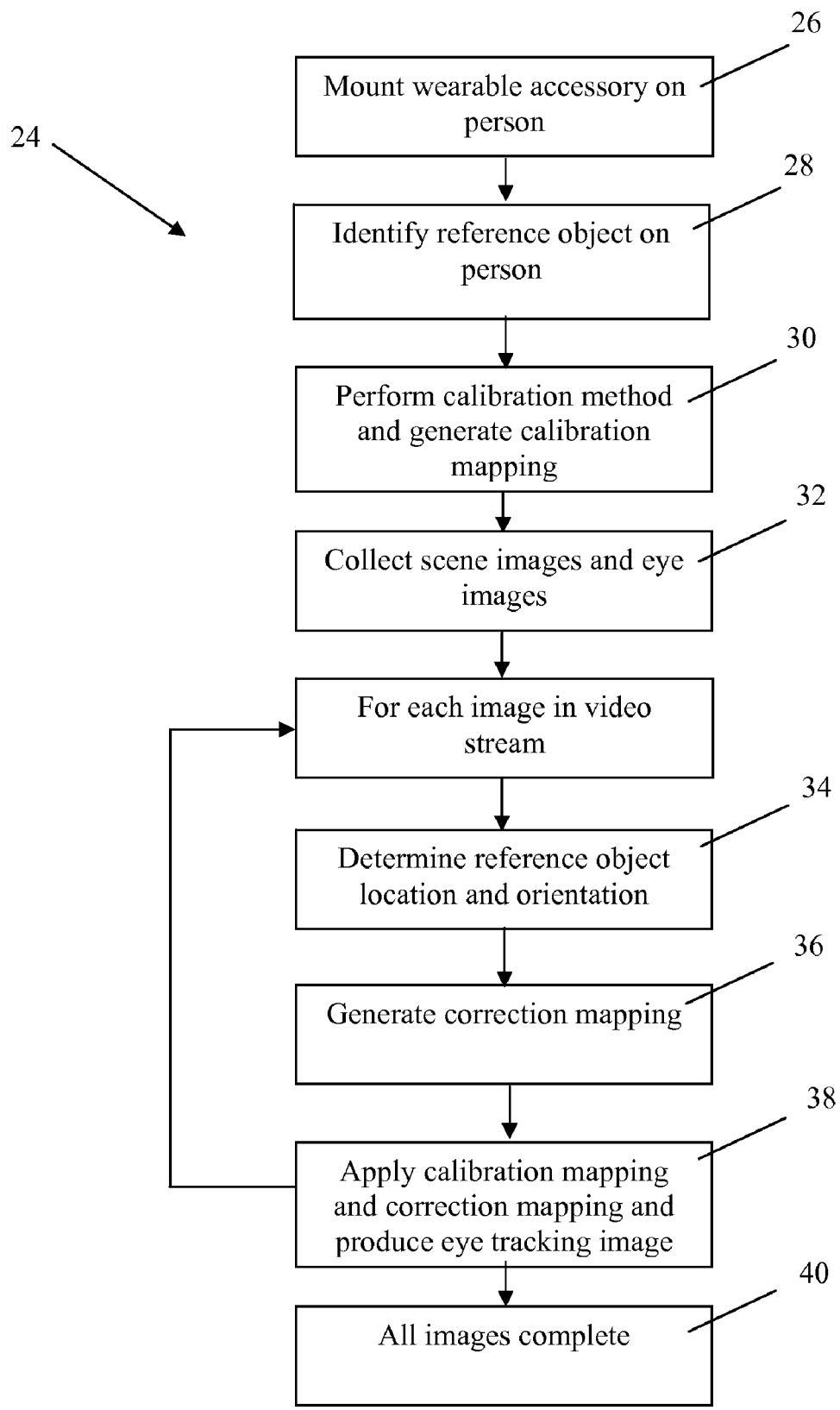
FIG. 2 is a flowchart depicting a method of correcting for movement of a reference object within an image detection field of an eye tracking apparatus according to an embodiment of the invention.

As shown in FIG. 2, the wearable accessory 16 is first mounted on the person and a reference object is identified, as indicated at steps 26 and 28. The reference object may be a naturally occurring facial landmark or an artificial landmark located within an image detection field of the eye camera 14. Naturally occurring landmarks are uniquely identifiable visible or invisible spectrum objects such as features of the eye, freckles, eye brows, veins or wrinkles, for example. Artificial landmarks include markers applied to the person's skin such as a cross-hair applied with an infrared ink pen or a sticker with visible patterns, for example. A single reference object may be identified on the person, or alternatively, more than one reference object may be identified on the person. In some applications, using more than one reference object provides for more accurate results by compensating for situations such as skin stretch, reference point occlusion and partially washed out reference markers, for example.

Figure 3:
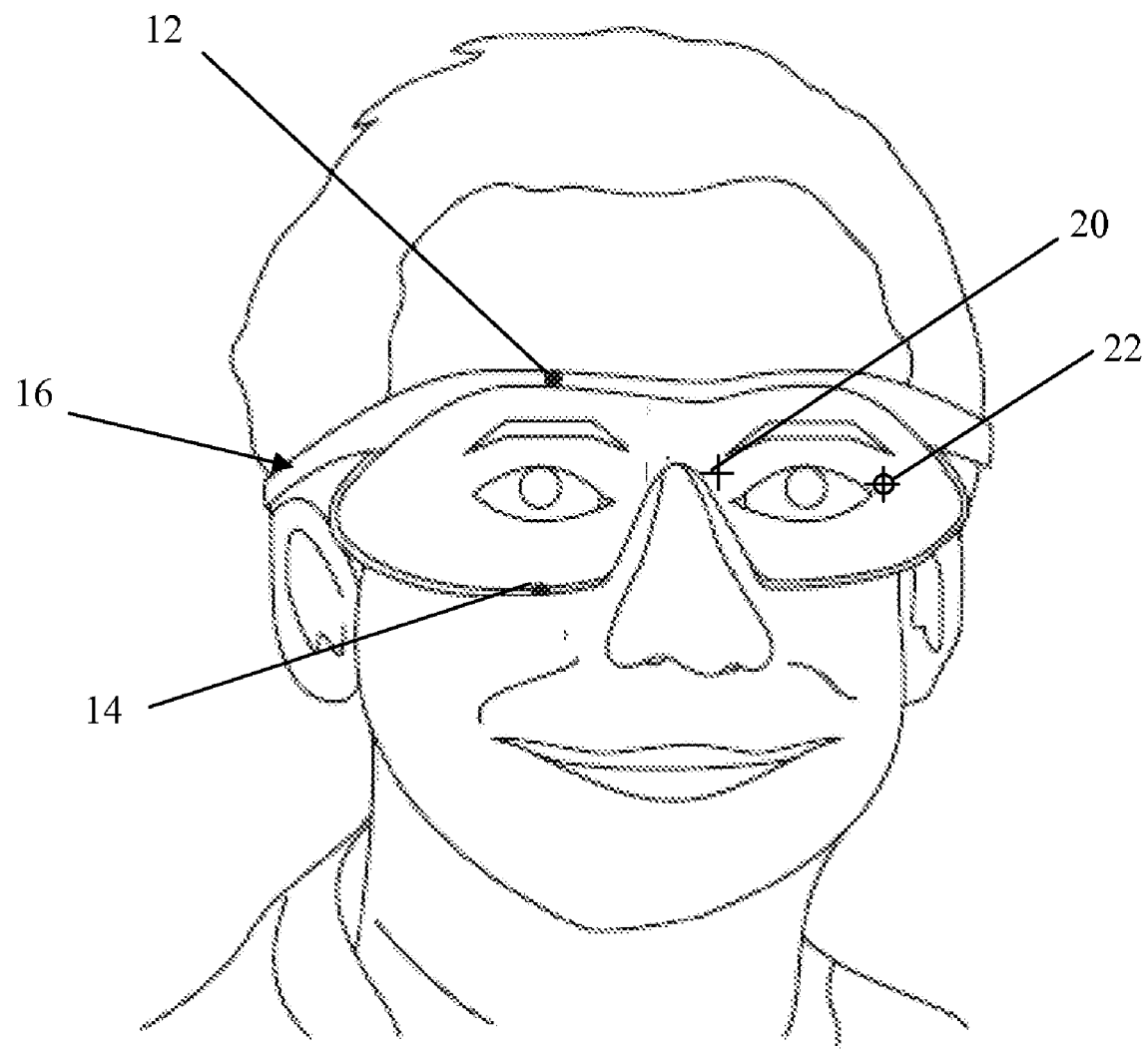
FIG. 3 is a front view of a wearable accessory of the eye tracking apparatus of FIG. 1 being worn by the person.

An example is shown in FIG. 3 in which first and second reference objects 20 and 22 that are placed on surrounding facial features of the person. The reference objects are artificial landmarks that are located within image detection field 42, which is shown in FIG. 5, and captured by the eye camera 14.

Referring back to FIG. 2, once one or more reference objects have been identified, a calibration method is performed and a calibration mapping is generated, as indicated at step 30. As part of the calibration method, a calibrated location and calibrated orientation of the reference object is stored in computer memory. The calibration method may be any known calibration method that maps pupil location within the image detection field of an eye image to a corresponding scene image. One example of a calibration method is shown in FIGS. 4(*a*), (*b*) and (*c*). In this example, the computer processor generates a calibration mapping based on calibration data obtained by having the person fixate successively on a series of numbers in a calibration grid while maintaining a steady head position. The calibration method will not be described further because this and other calibration methods are well known in the art.

Following generation of the calibration mapping, collection of eye tracking data, including eye images and scene images, begins, as indicated at step 32. For each image that is captured using the scene camera 12 and eye camera 14, a location and orientation of the reference object is determined, as indicated at step 34, and a correction mapping is generated, as indicated at step 36. The processor generates the correction mapping based on the location and orientation of the reference objects in each eye image relative to the calibrated location and calibrated orientation. The method of determining the location and orientation of the reference object may be any object recognition image processing method. Such methods are well known in the art and therefore will not be described further here.

Referring to FIG. 5, reference numerals 20' and 22' correspond to reference objects 20 and 22, respectively, of the example of FIG. 3. As shown, the reference objects 20', 22' have translated and rotated from the calibrated location and orientation that was determined at step 30. The translation and rotation of the reference objects 20, 22 is a result of movement of the wearable accessory 16 relative to the person. The movement may be due to a disturbance, such as being physically bumped, for example, or due to gradual shifting over time, such as glasses sliding down the nose of the person, or a helmet shifting on the head of the person, for example.

The correction mapping that defines the translation and rotation of the reference objects 20, 22 may be linear or non-linear. In the eye image of FIG. 5, reference object 20' has translated $\Delta x_1$ horizontally, translated $\Delta y_1$ vertically, and rotated $\theta_1$ from its calibrated location and calibrated orientation within the image detection field 42 and reference object 22' has translated $\Delta x_2$ horizontally, translated $\Delta y_2$ vertically, and rotated $\theta_2$ from its calibrated location and calibrated orientation within the image detection field 42.

Because the reference objects 20, 22 are facial landmarks or artificial landmarks that are applied to the person's skin, the reference objects 20, 22 may be fixed relative to one another or may move independently. Movement of the reference objects 20, 22 relative to one another may occur when the skin is distorted due to movement of facial muscles during facial expressions, such as a smile, for example. Such distortions may result in a non-linear correction mapping.

In addition, the type of camera lens of the scene camera 12 and eye camera 14 impacts whether the correction mapping is linear or non-linear. For example, when using a wide-angle lens, displacements near the edge of the image may appear smaller than similar displacements near the centre of the image.

Referring again to FIG. 2, the calibration mapping and correction mapping are then applied to each eye tracking image that is produced by the computer 20, as indicated at step 38. Once all of the images have been calibrated and corrected, as indicated at step 40, a single video stream including a gaze point that corresponds to an actual line of sight of the person for each frame may be produced.

In another embodiment, the correction mapping is combined with the calibration mapping prior to being applied to each eye tracking image. In this embodiment, a pre-disturbance calibration mapping is generated at step 30 and a post-disturbance calibration mapping, which is modified based on the correction mapping, is generated at step 36. At step 38, the post-disturbance mapping is applied during processing of the eye images and corresponding scene images.

In yet another embodiment, the second image detector 14 is replaced by a proximity detector. In this embodiment, the proximity detector captures frames of the person's eye and surrounding facial features and is able to track eye movement and reference object movement based on the distance from the proximity detector. In still another embodiment, the second image detector 14 is an image detector that tracks eye movement and reference object movement based on changes in profile. In this embodiment, the detector is located adjacent to the eye and the reference object is placed at a suitable location in the field of view of the image detector. The reference object may include a profile, such as a raised reference mark, for example.

It will be appreciated by a person skilled in the art that although the wearable accessory 16 shown in the figures is a pair of eye glasses, other wearable accessories may be used, such as a brimmed hat, a non-brimmed hat, a bicycle helmet, a football helmet or a camera boom, for example. Any accessory that allows the scene camera 12 to capture images from the point of view of the person while the eye camera captures corresponding images of the person's eye and surrounding facial features may be used.

One advantage of the method and apparatus for correcting for movement of a reference object within an image detection field of an eye tracking apparatus described herein is that subtle movement of the head-mounted accessory relative to the person may be detected. If the movement of the accessory is small, it may not be noticed by the person or nearby observers. Without the method and apparatus described herein, compromised eye tracking data may be collected inadvertently. Depending on the application of the eye tracking data, such compromised data could skew the outcome of scientific studies or marketing exercises, for example.

Another advantage of the method and apparatus for correcting for movement of a reference object within an image detection field of an eye tracking apparatus is that the person is able continue performing a task without taking a break to re-calibrate the eye tracking apparatus 10. Such a distraction may be highly disruptive if the person is fully engaged in a task such a sports game, scientific study, or medical operation.

Specific embodiments have been shown and described herein. However, modifications and variations may occur to those skilled in the art. All such modifications and variations are believed to be within the scope and sphere of the present invention.

The invention claimed is:

1. A method of correcting for movement of a reference object within an image detection field of an eye tracking apparatus said method comprising:
    providing said eye tracking apparatus, said eye tracking apparatus including a first image detector for capturing scene images, a second image detector for capturing eye images including a pupil of said person and a processor for receiving said scene images and said eye images and outputting eye tracking images, each of said eye tracking images including a gaze point corresponding to a line of sight of said person, said first image detector and said second image detector being coupled to a wearable accessory and being fixed relative to one another;
    mounting said wearable accessory on said person;
    identifying said reference object, said reference object being a marker applied to the skin of said person and being located within said image detection field of said second image detector;
    performing a calibration method and generating a calibration mapping, said calibration mapping for mapping pupil location within said image detection field to said scene images;
    capturing said scene images and said eye images;
    determining a location of said reference object within said image detection field on each of said eye images;
    applying said calibration mapping to each of said eye tracking images and adjusting said gaze point on each of said eye tracking images to correct for movement of said reference object within said image detection field;
    wherein movement of said reference object within said image detection field corresponds to movement of said wearable accessory relative to said person.

2. A computer-readable medium comprising instructions executable on a processor for implementing the method of claim 1.

3. A method of correcting for movement of a reference object within an image detection field of an eye tracking apparatus as claimed in claim 1, wherein said gaze point on each eye tracking image is adjusted based on a correction mapping.

4. A method of correcting for movement of a reference object within an image detection field of an eye tracking apparatus as claimed in claim 1, wherein said correction mapping defines a difference between a calibrated location and calibrated orientation of said reference object and a location and orientation of said reference object on each of said eye images.

5. A method of correcting for movement of a reference object within an image detection field of an eye tracking apparatus as claimed in claim 1, wherein said first image detector is a first video camera and said second image detector is a second video camera.

6. An eye tracking apparatus comprising:

a first image detector for capturing scene images;

a second image detector for capturing eye images including a pupil of a person and a reference object located within an image detection field, said second image detector being fixed relative to said first image detector and said reference object being a marker applied to the skin of said person;

a processor for receiving said scene images and said eye images and outputting eye tracking images, each of said eye tracking images including a gaze point corresponding to a line of sight of said person, said processor for determining a location of said gaze point based on a calibration mapping that maps pupil location within said image detection field to said scene images and a correction mapping that corrects for movement of said reference object within said image detection field of said second image detector;

wherein said first image detector and said second image detector are coupled to a wearable accessory and movement of said reference object within said image detection field corresponds to movement of said wearable accessory relative to said person.

7. An eye tracking apparatus as claimed in claim 6, wherein said first image detector is a first video camera and said second image detector is a second video camera.

8. An eye tracking apparatus as claimed in claim 6, wherein said correction mapping defines a difference between a calibrated location and calibrated orientation of said reference object and a location and orientation of said reference object on each of said eye images.

* * * * *